United States Patent
Parthasaradhi Reddy et al.

(10) Patent No.: US 8,445,506 B2
(45) Date of Patent: May 21, 2013

(54) POLYMORPHS OF LOPINAVIR

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Kesireddy Subash Chander Reddy, Hyderabad (IN)

(73) Assignee: Hetero Research Foundation (IN)

( * ) Notice: Subject to any disclaimer, the term of this patent is extended or adjusted under 35 U.S.C. 154(b) by 184 days.

(21) Appl. No.: 13/121,505

(22) PCT Filed: Feb. 6, 2009

(86) PCT No.: PCT/IN2009/000083
§ 371 (c)(1),
(2), (4) Date: May 10, 2011

(87) PCT Pub. No.: WO2010/089753
PCT Pub. Date: Aug. 12, 2010

(65) Prior Publication Data
US 2011/0294839 A1    Dec. 1, 2011

(51) Int. Cl.
*A61K 31/505*    (2006.01)
*C07D 239/10*    (2006.01)

(52) U.S. Cl.
USPC .......................................... 514/274; 544/316

(58) Field of Classification Search
USPC .......................................... 514/274; 544/316
See application file for complete search history.

(56) References Cited

U.S. PATENT DOCUMENTS 5,914,332 A    6/1999    Sham et al.

FOREIGN PATENT DOCUMENTS

| WO | 01/74787 A2 | 10/2001 |
| WO | 2006/100552 A1 | 9/2006 |
| WO | 2009004653 A2 | 1/2009 |

OTHER PUBLICATIONS

Written Opinion and International Search Report of of PCT/IN/2009/000083.

*Primary Examiner* — James O Wilson
*Assistant Examiner* — Ebenezer O Sackey
(74) *Attorney, Agent, or Firm* — Caesar, Rivise, Bernstein, Cohen & Pokotilow, Ltd.

(57) ABSTRACT

The present invention provides a novel cyclohexane solvate form of lopinavir, and a process for its preparation thereof. The present invention also provides a novel desolvated crystalline form of lopinavir, process for its preparation and to pharmaceutical composition containing it. Thus, for example, lopinavir cyclohexane solvate was heated at 100° C. for 10 hours to give lopinavir desolvated crystalline form H1.

18 Claims, 3 Drawing Sheets

POLYMORPHS OF LOPINAVIR

FIELD OF THE INVENTION

The present invention provides a novel cyclohexane solvate form of lopinavir, and a process for its preparation thereof. The present invention also provides a novel desolvated crystalline form of lopinavir, process for its preparation and to pharmaceutical composition containing it.

BACKGROUND OF THE INVENTION

Inhibitors of human immunodeficiency virus (HIV) protease have been approved for use in the treatment of HIV infection for several years. A particularly effective HIV protease inhibitor is (2S,3S,5S)-2-(2,6-dimethylphenoxyacetyl) amino-3-hydroxy-5-(2-1-tetrahydropyrimid-2-onyl)-3-methylbutanoyl)amino-1,6-diphenylhexane, also known as Lopinavir. Lopinavir is represented by the following structure.

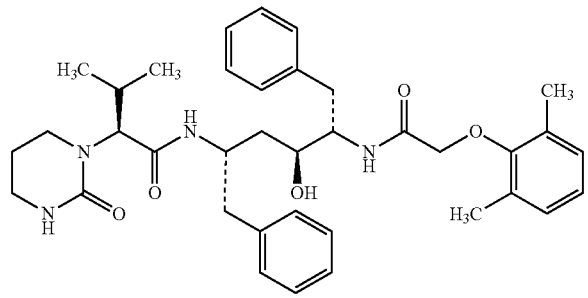 [SMILES: Cc1cccc(C)c1OCC(=O)N[C@@H](Cc1ccccc1)[C@@H](O)C[C@H](Cc1ccccc1)NC(=O)[C@H](C(C)C)N1CCCNC1=O]

Lopinavir is known to have ability of inhibiting HIV protease and the HIV infection. Lopinavir is particular effective for the inhibition of HIV protease and for the inhibition of HIV infection when co administered with Ritonavir.

Lopinavir may be prepared using the procedures described in U.S. Pat. No. 5,914,332. This patent also disclosed a process for the preparation of amorphous lopinavir.

Pharmaceutical compositions comprising lopinavir or a pharmaceutically acceptable salt thereof were disclosed in U.S. Pat. No. 5,914,332.

Polymorphism is defined as "the ability of a substance to exist as two or more crystalline phases that have different arrangement and/or conformations of the molecules in the crystal Lattice. Thus, in the strict sense, polymorphs are different crystalline forms of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning Calorimetry (DSC) and Infrared spectrometry (IR).

Solvent medium and mode of crystallization play very important role in obtaining a crystalline form over the other.

Lopinavir can exist in different polymorphic forms, which differ from each other in terms of stability, physical properties, spectral data and methods of preparation.

WO Patent Publication No. 2001/74787 (herein after referred to as the '787 patent publication) described various polymorphic forms of lopinavir and processes for their preparation. The Publication described the formation of several polymorphic forms of lopinavir, which were designated lopinavir crystal form of Type I hydrated, Type I higher hydrated, Type II isopropanol hemisolvate, Type II isopropanol solvate, Type II ethyl acetate hemisolvate, Type II ethyl acetate solvate, Type II chloroform hemisolvate, Type III ethyl acetate solvated, Type III desolvated and Type IV non-solvated.

According to the '787 patent publication, Type I hydrated crystal form of lopinavir (characterized by an X-ray powder diffraction pattern having peaks expressed as 2θ at about 7.25, 8.53, 10.46, 11.05, 11.71, 14.76, 15.30, 16.67, 17.32, 19.10, 19.57, 21.24, 21.84 and 22.46±0.1 degrees) can be prepared by crystallization of lopinavir from solution or suspension in water or from solutions in mixtures of water and water miscible organic solvents such as methanol, ethanol and acetonitrile.

According to the '787 patent publication, Type I higher hydrated crystal form of lopinavir (characterized by an X-ray powder diffraction pattern having peaks expressed as 2θ at about 3.89, 6.55, 7.76, 8.55, 9.70, 10.56, 14.76, 15.57, 18.30, 18.95 and 22.74±0.1 degrees) can be prepared by crystallization of hydrated lopinavir from a warm solution in a mixture of water and ethanol, followed by extended exposure to an elevated relative humidity environment.

According to the '787 patent publication, Type III ethyl acetate solvated crystal form of lopinavir (characterized by an X-ray powder diffraction pattern having peaks expressed as 2θ at about 4.85, 6.52, 7.32, 12.82, 12.96, 16.49 and 19.31±0.1 degrees) can be prepared by slow addition of an heptane to a heated solution of lopinavir in the ethyl acetate, thereby inducing crystallization and then isolation by filtration.

According to the '787 patent publication, Type III desolvated crystal form of lopinavir (characterized by an X-ray powder diffraction pattern having peaks expressed as 2θ at about 4.85, 6.39, 7.32, 8.81, 12.20, 12.81, 14.77, 16.45 and 17.70±0.1 degrees, and the DSC thermogram having a melting endotherm with onset at 95 deg C. and peak at 98 deg C.) can be prepared by crystallization from acetonitrile.

According to the '787 patent publication, Type IV non-solvated crystal form of lopinavir (characterized by an X-ray powder diffraction pattern having peaks expressed as 2θ at about 6.85, 9.14, 12.88, 15.09, 17.74, 18.01 and 18.53±0.1 degrees, and the DSC thermogram having a melting endotherm with onset at 117 deg C. and peak at 122 deg C.) can be prepared from acetonitrile by slow cooling and slow evaporation of a saturated solution or by exposure of amorphous lopinavir to an acetonitrile atmosphere.

WO Patent Publication No. 2009/004653 disclosed a process for preparing an amorphous form of lopinavir.

We have discovered a stable novel desolvated crystalline form of lopinavir and cyclohexane solvate of lopinavir.

One object of the present invention is to provide a novel cyclohexane solvate form of lopinavir and a process for preparing it.

According to another object of the present invention is to provide a novel desolvated crystalline form of lopinavir and a process for preparing it.

Still another object of the present invention is to provide pharmaceutical composition of a novel desolvated crystalline form of lopinavir.

SUMMARY OF THE INVENTION

In accordance with one aspect of the present invention, there is provided lopinavir cyclohexane solvate, characterized by peaks in the powder x-ray diffraction spectrum having 2θ angle positions at about 4.9, 7.4, 13.4, 14.6, 17.5, 18.9 and 23.8±0.2 degrees.

In accordance with another aspect of the present invention, there is provided a process for preparing lopinavir cyclohexane solvate which comprises:
  a) dissolving lopinavir in an organic solvent;
  b) removing the solvent from the solution obtained in step (a) to obtain a residue.
  c) slurrying the residue obtained in step (b) with cyclohexane solvent; and
  d) isolating lopinavir cyclohexane solvate.

In accordance with another aspect of the present invention, there is provided a novel desolvated crystalline form of lopinavir designated as form H1 characterized by peaks in the powder x-ray diffraction spectrum having 2θ angle positions at about 5.6, 8.6, 13.8, 14.3, 19.2 and 19.5±0.2 degrees.

In accordance with another aspect of the present invention, there is provided a process for the preparation of lopinavir desolvated crystalline form H1, which comprises heating lopinavir cyclohexane solvate at above 80 deg C.

In accordance with another aspect of the present invention, there is provided a pharmaceutical composition comprising lopinavir desolvated crystalline form H1 and a pharmaceutically acceptable excipient.

DETAILED DESCRIPTION OF THE INVENTION

In accordance with one aspect of the present invention, there is provided lopinavir cyclohexane solvate, characterized by peaks in the powder x-ray diffraction spectrum having 2θ angle positions at about 4.9, 7.4, 13.4, 14.6, 17.5, 18.9 and 23.8±0.2 degrees. The powdered x-ray diffractogram (PXRD) of lopinavir cyclohexane solvate is shown in FIG. 1.

In accordance with another aspect of the present invention, there is provided a process for preparing lopinavir cyclohexane solvate which comprises:
  a) dissolving lopinavir in an organic solvent;
  b) removing the solvent from the solution obtained in step (a) to obtain a residue.
  c) slurrying the residue obtained in step (b) with cyclohexane solvent; and
  d) isolating lopinavir cyclohexane solvate.

The organic solvent used in step (a) is a solvent or mixture of solvents selected from the group consisting of a chlorinated solvent, an alcoholic solvent and a ketonic solvent. Preferable organic solvent is selected from dichloromethane, methanol, ethanol and acetone, still more preferable organic solvent is dichloromethane.

The distillation of the solvent may be carried out at atmospheric pressure or at reduced pressure. The distillation may also preferably be carried out until the solvent is almost completely distilled off.

The temperature at which slurrying is carried out is not critical and the slurrying may conveniently be carried out at room temperature.

The isolation of lopinavir cyclohexane solvate may be performed by conventional techniques such as centrifugation and filtration.

Lopinavir used in the process of the present invention may be in the form of hydrated, non-solvated, amorphous, desolvated or solvated lopinavir. Thus, for example, lopinavir amorphous form, lopinavir crystal form of type I hydrated, lopinavir crystal form of type I higher hydrated, lopinavir crystal form of type III ethyl acetate solvated, lopinavir crystal form of type III desolvated and lopinavir crystal form of type IV non-solvated may be used.

It has surprisingly been found that steps (a) and (b) are also required for obtaining lopinavir cyclohexane solvate.

In accordance with another aspect of the present invention, there is provided a novel desolvated crystalline form of lopinavir designated as form H1 characterized by peaks in the powder x-ray diffraction spectrum having 2θ angle positions at about 5.6, 8.6, 13.8, 14.3, 19.2 and 19.5±0.2 degrees. The powdered x-ray diffractogram (PXRD) of lopinavir desolvated crystalline form H1 is shown in FIG. 2.

Lopinavir desolvated crystalline form H1 of present invention is further characterized by a Differential Scanning Calorimetry (DSC) thermogram as shown in FIG. 3.

The DSC thermogram of the lopinavir desolvated crystalline form H1 exhibits a melting small endotherm at about 111 deg C. followed by a sharp endotherm at about 115 deg C. when differential scanning calorimetry is performed with a scanning rate of 1 deg C. per minute from 50 deg C. to 150 deg C.

It has surprisingly been found that a novel lopinavir desolvated crystalline form H1 can be obtained simply by heating the novel lopinavir cyclohexane solvate. Thus, the novel lopinavir cyclohexane solvate constitutes useful intermediate for preparing the novel lopinavir desolvated crystalline form H1.

In accordance with another aspect of the present invention, there is provided a process for the preparation of lopinavir desolvated crystalline form H1, which comprises heating lopinavir cyclohexane solvate at above 80 deg C.

Preferably heating may be performed at 80 deg C. to 120 deg C. The heating may be carried out until lopinavir cyclohexane solvate is completely converted into lopinavir desolvated crystalline form H1.

In accordance with another aspect of the present invention, there is provided a pharmaceutical composition comprising lopinavir desolvated crystalline form H1 and a pharmaceutically acceptable excipient.

Preferable pharmaceutical composition of lopinavir desolvated crystalline form H1 is an oral dosage form, comprising lopinavir desolvated crystalline form H1.

Figure 1:
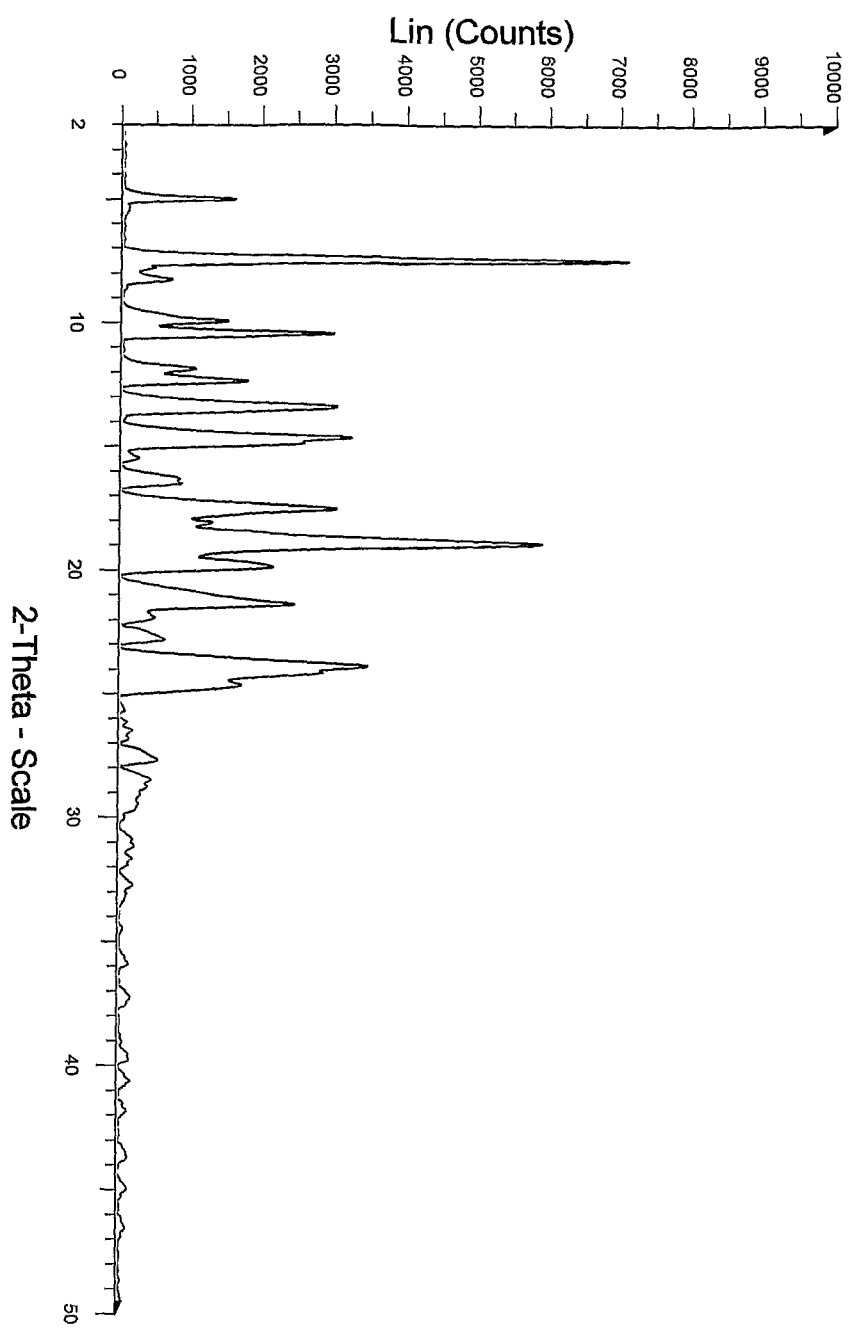
FIG. 1 is X-ray powder diffraction spectrum of lopinavir cyclohexane solvate.

X-ray powder diffraction spectrum was measured on a bruker axs D8 advance X-ray powder diffractometer having a copper-Kα radiation. Approximately 1 gm of sample was gently flattered on a sample holder and scanned from 2 to 50 degrees two-theta, at 0.03 degrees to theta per step and a step of 0.5 seconds. The sample was simply placed on the sample holder. The sample was rotated at 30 rpm at a voltage 40 KV and current 35 mA.

DSC (Differential Scanning Calorimetry) measurements were performed with a DSC Q10 (TA Instruments, Inc.). About 3 mg of the powder was placed in an open aluminum pan and it was crimped with an aluminum lid. The crimped sample was then placed in the DSC cell opposite to empty aluminum pan (as reference) and the sample was scanned at 1 deg C./min from 50 deg C. to 150 deg C.

The invention will now be further described by the following examples, which are illustrative rather than limiting.

EXAMPLES

Example 1

Thionyl chloride (18 ml) was added to the mixture of 2S-(1-tetrahydropyrimid-2-onyl)-3-methylbutanoic acid (25 gm), tetrahydrofuran (370 ml) and dimethylformamide (2 ml) at 0-10 deg C. and the mass was stirred for 1 hour 15 minutes. The mass was subjected to distillation under reduced pressure to remove excess thionyl chloride, n-heptane (45 ml) was added to the residue obtained and the solvent was distilled off. The reaction mass was slurried in dimethylformamide (105 ml). (2S,3S,5S)-2-(2,6-dimethylphenoxyacetyl)amino-3-hydroxy-5-amino-1,6-diphenylhexane (41 gm), imidazole (25 gm) and 4-(dimethylamino)pyridine (1.5 gm) were dissolved in ethyl acetate (420 ml). To the solution was added above slurried product at 0-10 deg C. The reaction mass was maintained for 14 hours and then ethyl acetate (165 ml) and water (250 ml) were added. The layers were separated, water (250 ml) was added to the organic layer and the pH was adjusted to 2.0-3.0 with dilute hydrochloric acid (6N HCl). The layers were separated, the organic layer was washed with aqueous sodium bicarbonate and then with water. The ethyl acetate was distilled off from the mass. The reaction mass was dissolved in ethyl acetate (80 ml) and n-heptane (80 ml) was added to the solution. The separated solid was stirred with ethyl acetate (290 ml) for 8 hours, filtered and dried the solid to obtain 33 gm of lopinavir ethyl acetate solvate.

Example 2

Lopinavir ethyl acetate solvate (5 gm) obtained as in example 1 was dissolved in dichloromethane (50 ml), methylenedichloride layer was dried over sodium sulfate and distilled off the solvent under vacuum at 45 deg C. to obtain residue. Cyclohexane (20 ml) was added to the residue, distilled off the solvent and the residue was collected. The residue obtained was taken in cyclohexane (40 ml), stirred for 60 hours at 20-25 deg C., filtered, washed the solid with cyclohexane (10 ml) and dried at 55-60 deg C. for 3 hours to obtain 5 gm of lopinavir cyclohexane solvate.

Example 3

Lopinavir ethyl acetate solvate (5 gm) obtained as in example 1 was dissolved in acetone (45 ml), acetone layer was dried over sodium sulfate and distilled off the solvent under vacuum at 45 deg C. to obtain residue. Cyclohexane (20 ml) was added to the residue, distilled off the solvent and the residue was collected. The residue obtained was taken in cyclohexane (35 ml), stirred for 60 hours at 20-25 deg C., filtered, washed the solid with cyclohexane (10 ml) and dried at 55-60 deg C. for 3 hours to obtain 4.8 gm of lopinavir cyclohexane solvate.

Example 4

Lopinavir (10 gm) was dissolved in dichloromethane (90 ml), methylenedichloride layer was dried over sodium sulfate and distilled off the solvent under vacuum at 45 deg C. to obtain residue. To the residue was added cyclohexane (50 ml), distilled off the solvent and the residue was collected. The residue obtained was taken in cyclohexane (70 ml), stirred for 60 hours at 20-25 deg C., filtered, washed the solid with cyclohexane (20 ml) and dried at 55-60 deg C. for 4 hours to obtain 9.5 gm of lopinavir cyclohexane solvate.

Example 5

Lopinavir cyclohexane solvate (5 gm) obtained as in example 2 was heated at 90 deg C. for 15 hours to obtain 4.2 gm of lopinavir desolvated crystalline form H1.

Example 6

Lopinavir cyclohexane solvate (5 gm) obtained as in example 2 was heated at 100 deg C. for 10 hours to obtain 4.3 gm of lopinavir desolvated crystalline form H1.

We claim:

1. A lopinavir cyclohexane solvate, characterized by an X-ray powder diffractogram having peaks expressed as 2θ angle positions at about 4.9, 7.4, 13.4, 14.6, 17.5, 18.9 and 23.8±0.2 degrees.

2. A lopinavir cyclohexane solvate, characterized by an x-ray powder diffractogram as shown in FIG. 1.

3. A process for the preparation of lopinavir cyclohexane solvate as defined in claim 1, which comprises:
   a. dissolving lopinavir in an organic solvent;
   b. removing the solvent from the solution obtained in step (a) to obtain a residue.
   c. slurrying the residue obtained in step (b) with cyclohexane solvent; and
   d. isolating lopinavir cyclohexane solvate.

4. The process as claimed in claim 3, wherein the solvent used in step (a) is a solvent or mixture of solvents selected from a chlorinated solvent, an alcoholic solvent and a ketonic solvent.

5. The process as claimed in claim 4, wherein the organic solvent used in step (a) is selected from dichloromethane, methanol, ethanol and acetone.

6. The process as claimed in claim 4, wherein the organic solvent used in step (a) is dichloromethane.

7. The process as claimed in claim 3, wherein the slurring in step (c) is carried out at room temperature.

8. The process as claimed in claim 3, wherein the lopinavir used is in the form of hydrated, non-solvated, amorphous, desolvated or solvated lopinavir.

9. The process as claimed in claim 8, wherein the lopinavir used is in the form of lopinavir amorphous form, lopinavir crystal form of type I hydrated, lopinavir crystal form of type I higher hydrated, lopinavir crystal form of type III ethyl acetate solvated, lopinavir crystal form of type III desolvated and lopinavir crystal form of type IV non-solvated.

10. A lopinavir desolvated crystalline form H1, characterized by an X-ray powder diffractogram having peaks expressed as 2θ angle positions at about 5.6, 8.6, 13.8, 14.3, 19.2 and 19.5±0.2 degrees.

Figure 2:
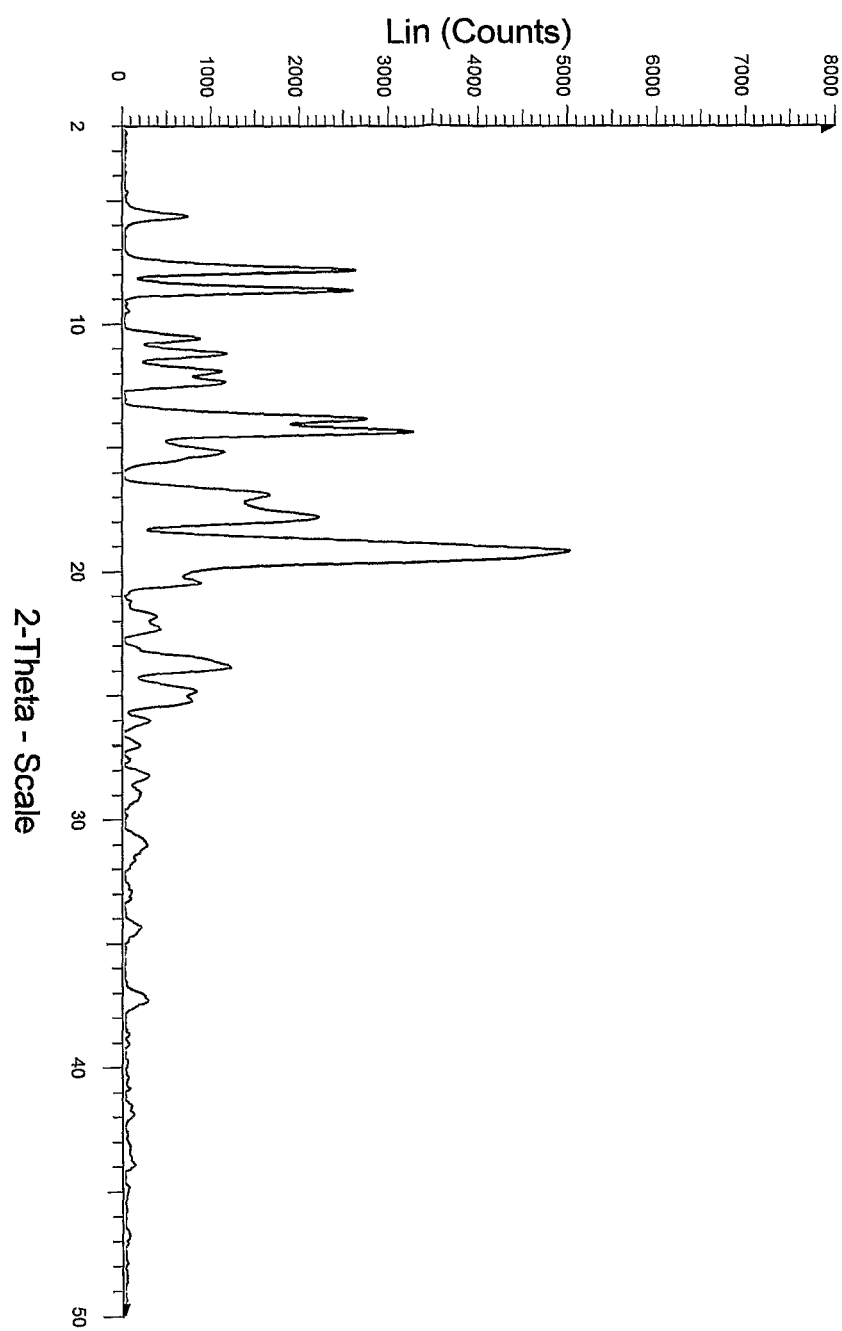
FIG. 2 is X-ray powder diffraction spectrum of lopinavir desolvated crystalline form H1.

11. A lopinavir desolvated crystalline form H1, characterized by an x-ray powder diffractogram as shown in FIG. 2.

Figure 3:
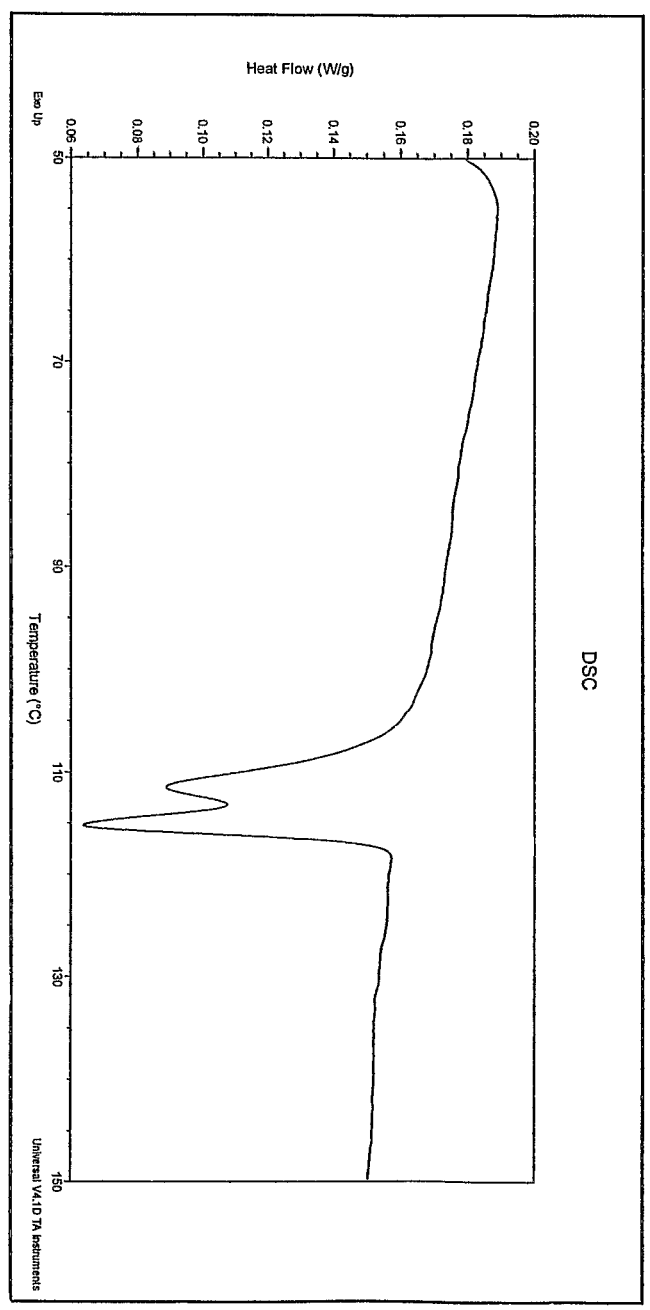
FIG. 3 is Differential scanning calorimetry (DSC) thermogram of lopinavir desolvated crystalline form H1.

12. The lopinavir desolvated crystalline form H1 as claimed in claim 10, wherein the lopinavir desolvated crystalline form H1 is further characterized by a differential scanning calorimetry thermogram as shown in FIG. 3.

13. The process as claimed in claim 12, wherein the lopinavir desolvated crystalline form H1 having a melting small endotherm at about 111 deg C. followed by a sharp endotherm at about 115 deg C.

14. A process for the preparation of lopinavir desolvated crystalline form H1 as defined in claim 10, which comprises heating lopinavir cyclohexane solvate at above 80 deg C.

15. The process as claimed in claim 14, wherein the heating is carried out at about 80 deg C. to 120 deg C.

16. A pharmaceutical composition comprising lopinavir desolvated crystalline form H1 of claim 10 and a pharmaceutically acceptable excipient.

17. The pharmaceutical composition as claimed in claim 16, wherein the pharmaceutical composition of lopinavir desolvated crystalline form H1 is an oral dosage form.

18. The pharmaceutical composition as claimed in claim 17, wherein the oral pharmaceutical dosage forms is a tablet, a solution or a capsule.

* * * * *